(12) United States Patent
Jaworski

(10) Patent No.: US 8,177,856 B2
(45) Date of Patent: May 15, 2012

(54) HUMANLIKE MECHANICAL FINGER FOR PROSTETHIC HANDS AND MASSAGING DEVICE WITH HUMANLIKE MECHANICAL FINGERS

(76) Inventor: Edward Jaworski, Delta (CA)

( * ) Notice: Subject to any disclaimer, the term of this patent is extended or adjusted under 35 U.S.C. 154(b) by 101 days.

(21) Appl. No.: 12/655,244

(22) Filed: Dec. 28, 2009

(65) Prior Publication Data

US 2011/0160873 A1    Jun. 30, 2011

(51) Int. Cl.
*A61F 2/54* (2006.01)
*A61F 2/68* (2006.01)

(52) U.S. Cl. ........................................................ 623/64
(58) Field of Classification Search ................ 623/63–64
See application file for complete search history.

(56) References Cited

U.S. PATENT DOCUMENTS

| | | | | |
|---|---|---|---|---|
| 809,797 A * | 1/1906 | Grogan | ........................... | 623/63 |
| 2,435,614 A * | 2/1948 | Tureman, Jr. | ................... | 623/64 |
| 2,457,305 A * | 12/1948 | Dale | .............................. | 623/26 |
| 3,694,021 A * | 9/1972 | Mullen | ........................ | 294/106 |
| 4,466,800 A * | 8/1984 | Breiden | ........................ | 434/267 |
| 4,685,929 A * | 8/1987 | Monestier | ...................... | 623/64 |
| 4,986,723 A * | 1/1991 | Maeda | ......................... | 414/729 |
| 7,153,282 B1 * | 12/2006 | Dudley | .......................... | 601/93 |
| 2011/0144770 A1 * | 6/2011 | Moyer et al. | ................... | 623/64 |

* cited by examiner

*Primary Examiner* — Bruce E Snow

(57) ABSTRACT

A mechanical finger which visually and functionally resembles a human finger. The finger consists of three phalanges pivoted in their clevises. The first phalange is driven by a rod located in an arm and being connected to an actuator. The second and third phalanges are driven by tendons. The tension of the second phalange tendon is initiated by the movement of the first phalange and the tension of the third phalange tendon is initiated by the movement of the second phalange.

6 Claims, 4 Drawing Sheets

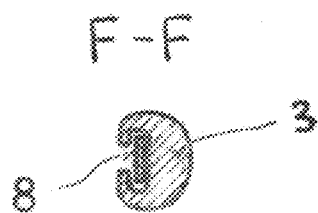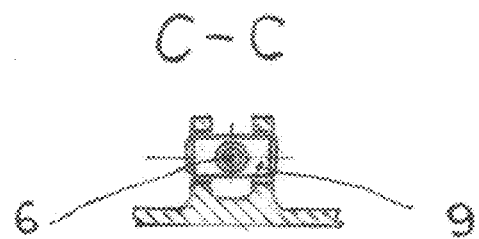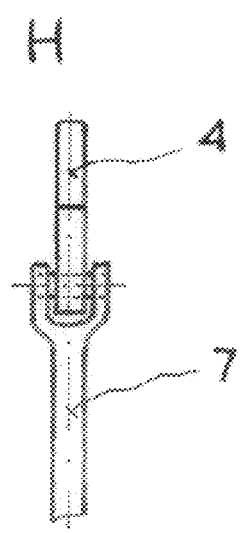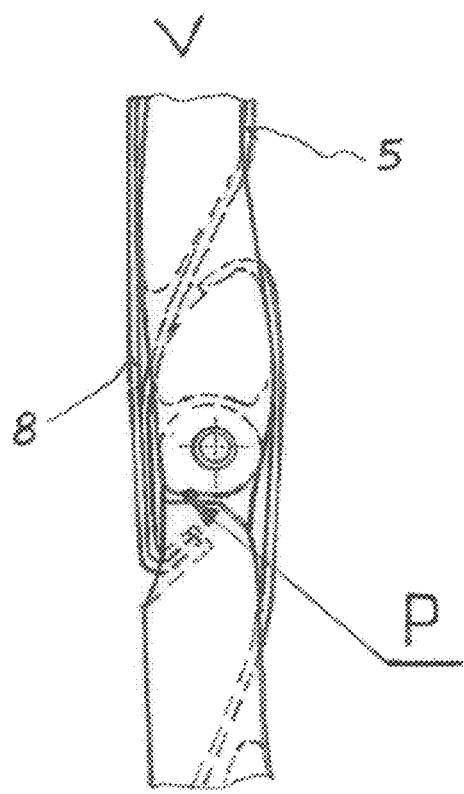

HUMANLIKE MECHANICAL FINGER FOR PROSTETHIC HANDS AND MASSAGING DEVICE WITH HUMANLIKE MECHANICAL FINGERS

BACKGROUND OF THE INVENTION

Author of the invention while at occupational therapy has noticed that human fingers are the most efficient tools in performing massaging therapy on damaged tissues around the scars. Among many available massaging devices one with the humanlike fingers is missing. Work on the project produced massaging device prototype with two unbendable fingers. Their massaging action was not as good though as an action of the straight thumb and bendable index finger or middle finger. Successful design of bendable finger has revealed a great opportunity for using it in the future development of the prosthetic hands. Upon review of the previous US patents in the field of mechanical fingers, hands and grasping devices and comparing their fingers and palm designs to the one presented here it becomes apparent that presented here solutions can make a real progress in creating practical and affordable prosthetic hand. Most of the previous designs are complicated, expensive and they give very little if any consideration to the esthetic side of the prosthesis. Those designs are more suitable for the robotic rather than for the human applications with exception of the few argued below. U.S. Pat. No. 4,685,929 J. Monestier. This invention provides soft gripping hand with the fingers of attractive humanlike appearance. However a fingers comprising of such a high number of elements would be very difficult or impossible to manufacture in humanlike dimensions. The other disadvantage would be their high cost. Another U.S. Pat. No. 7,655,051, M. Stark provides prosthetic hand with fingers biased in a closed position by springs and digits are opened by a cord attached to the dorsal side of the top digit. In this design gripping force of digits depends on the strength of a springs and it is believed that fingers would lose their humanlike size with the larger springs guaranteed a decent grip. Also it is hard to predict which phalange will start moving first upon release of the cord what would cause grips to be rather uncontrollable. The most appealing solutions for making a simple and inexpensive prosthetic hand are those by Frank L. Dale, U.S. Pat. No. 2,457,305. Dale teaches that it is possible to create prosthetic finger using just one element as a driving rod to bend finger and as a spring to straighten a finger. In my invention finger bending and straightening motion needs four elements a driving rod two tendons and a spring and although Dale's design is more simple it carries some crucial limitations compare to the design presented here; a) a digits of Dale's fingers need more space in front to place there a channel for a rod/spring element and fingers humanlike appearance may be compromised b) finger's bending motion will always start from the top digit contrary to the human fingers where all three digits are moving at the same time and while making most common grasping motion the Dale's fingers will have a tendency to slide off an objects attempted to be grasped from the top c) not having any adjustable elements to the finger's digits is a greatest limitation to Dale's finger comparing to my design where the middle digit's motion is regulated by the length of a first tendon or by an adjustable rod what allows to create a variety of prosthetic hands with different grips complementing individual needs as well as allowing to use finger in other applications like that in presented here massaging device where Dale's fingers would work improperly by pinching top portion of the flesh with a top digits instead of engaging larger portion of a fingers with a wider and deeper portion of the human body. Prosthetic hand with presented here fingers will not only look like the real one but will be able to perform a few simple tasks in it basic form as well as multiple tasks in it most developed and computerized form.

References Cited

| U.S. Patent Documents | | |
|---|---|---|
| 3,694,021 | September 1972 | Mullen |
| 3,866,966 | February 1975 | Skinner, II |
| 3,927,424 | December 1975 | Itoh |
| 4,377,305 | March 1983 | Horvath |
| 4,834,443 | May 1989 | Crowder et al. |
| 4,980,626 | December 1990 | Hess et al. |
| 4,984,951 | January 1991 | Jameson |
| 4,986,723 | January 1991 | Maeda |
| 5,080,681 | January 1992 | Erb |
| 5,108,140 | April 1992 | Bartholet |
| 5,200,679 | April 1993 | Graham |
| 5,280,981 | January 1994 | Schulz |
| 5,378,033 | January 1995 | Guo et al. |
| 5,762,390 | June 1998 | Gosselin et al. |

SUMMARY OF THE INVENTION

Presented here finger is operated by the rods, tendons and springs. Compacted design of the finger allows having it in the natural size and be covered by a flesh imitator. Applications are versatile and allow creating variations of the prosthetic hands in order to satisfy individual needs of amputees. The most basic and most affordable design of the prosthetic hand would be the one with the second phalanges adjustable rods being anchored in the arm and inactive after choosing desirable tension to the first tendon and giving the biggest slack to the thumb or adjustable rods being abandon altogether and the first tendons anchored to the back of the palm below the first phalange after deciding on the proper length of the tendons. All of the first phalanges activating rods would be connected to the one common element which would be activated one way only by the pneumatic pressure preferably and being pushed back by the spring upon the release. This hand would perform a basic grasping grip and assist amputees in the simple tasks like holding a steering wheel, a joystick, a hand bag, a glass, a railing and as such. The hand opening and closing button would be operated by the toe as an example. The last and the most developed form of the prosthetic hand would be the one with most of the rods connected to the separate actuators operated by servomotors or solenoids. The computer chip would allow activating a combination of different rods and performing different grips on the voice command . . . For example command "SPOON" would first activate driving rods of pinky, ring, and the middle finger to close them partially and activate afterwards driving rod of the index finger and the thumb as well as the thumb adjusting rod to give more slack to its first tendon. The commands "PEN" or "PINCH" would perform the same or very similar grip. On the command "PIANO" all fingers would bend except for the index finger which would be kept straight to perform typing like tasks. In the middle between basic and the most developed forms of prosthetic hands there would be some special order designs with only few actuators to perform selected tasks or some custom made like for example one with the first phalanges pivoting ears being positioned on the palm with slightly bigger angles between them so the fingers in the open position will be spread more apart to perform task of grasping larger, grapefruit like objects. All variations of prosthetic hands will use the same unchangeable elements. Similar elements can be also used for the wrist design. Just two more ears added at the base of the arm, two more clevises in the palm, connecting pins and the driving rod. Presented here massaging device can be easily mounted not only in the back of the chair as shown on the drawing but also can be accommodated into other structures like benches, mats and as a such with the purpose to use it in the spas, gyms, physiotherapy clinics as a multiple massaging units. It can be also used as a single unit being hold in one hand and providing massage to the different parts of the body and most likely being used as a masseur's helper. The other possible applications will be explained in the description of the drawings.

BRIEF DESCRIPTION OF THE DRAWINGS

FIG. 3 is the side view of the phalange 1 and the phalange 2.
FIG. 4 is the back view on the adjustable rod and the lower end of the first tendon.
FIG. 5 is the section through the guiding pin.
FIG. 6 is the cross section of the third phalange.

DETAILED DESCRIPTION OF THE INVENTION

FIG. 1

Figure 2:
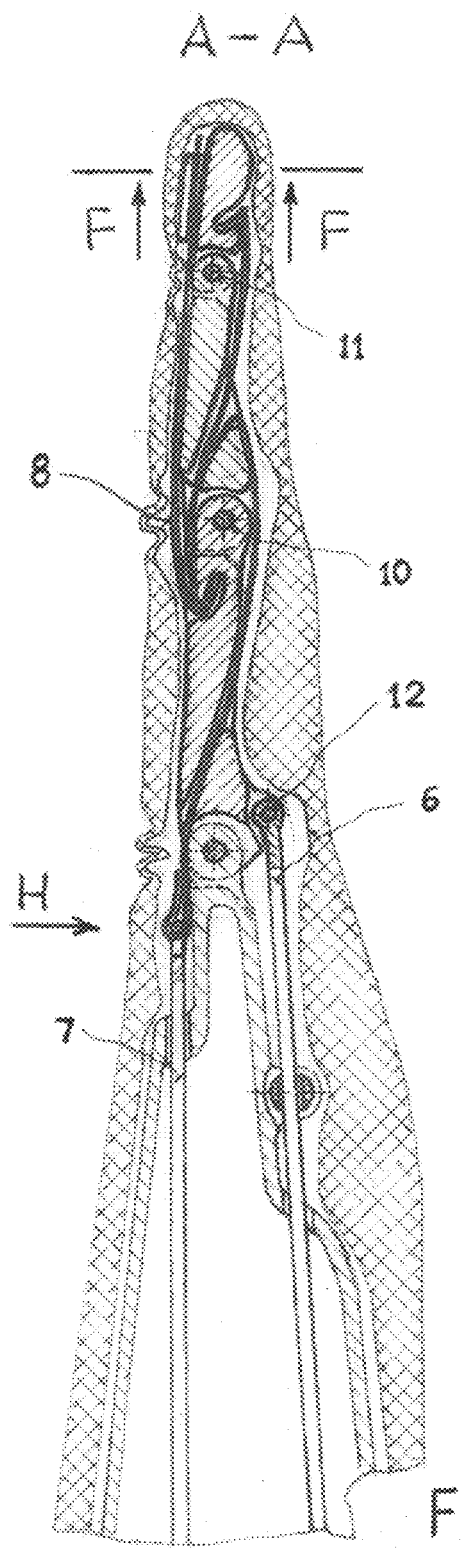
FIG. 2 is the main section of the finger.

It shows first phalange 1, second phalange 2, third phalange 3, first tendon 4, second tendon 5, activating rod 6 and rod's guiding pin 9. Each phalange has a clevis at one end and one ear at the other end. Guiding pin 9 is placed with loose in the round holes made across the ears placed on the palm structure and has a role to allow side movements of the upper part of the rod while restricting undesirable side movements of the lower part of the rod. The driving rod protrudes with the loose through the hole made across said pin 9. This will allow for the unrestricted up and down movement of the driving rod. On the palm structure are shown two more single ears for mounting the neighboring fingers.

FIG. 2

It shows all elements and describes the mechanics of the presented invention. It shows driving rod 6 placed in the clevis of the first phalange 1 and connected to that phalange by the pin 12 which is press fitted in the clevis and loose in the rod. In the middle of the first phalange 1 there is an opening through which protrudes firs tendon 4. Said tendon 4 can be anchored to the back of the palm structure or, as shown here, can be connected to the adjustable rod 7. The other end of the tendon 4 is firmly connected to the front of the second phalange 2 by an any means of the firm connection, and depending on the materials used, it can be glued, thermo integrated with the second phalange's material, connected by a mechanical fasteners and as such. The same connection applies to the both ends of the second tendon 5 which is permanently anchored to the back of the first phalange, protrudes through the middle opening of the second phalange and is firmly connected to the front of the third phalange 3. The similar fastening will also apply to the lower end of the flat spring 8 which is permanently connected to the back of the first phalange. The upper end of said spring 8 protrudes through the slot placed at the back of the third phalange. The role of the spring is to straighten second and third phalanges upon up movement of the rod 6. The spring can be single flat or multiple flats depending on the version of the prosthetic hand and the flexibility of the flesh imitating material. Pins 10 connect firs phalange to the palm structure and the second phalange to the first phalange. The smaller pin 11 connects phalange 3 with phalange 2. The pins are press fitted in the devises and having a loose in the ears. Upon the movement of the first phalange initiated by the down moving rod 6 the first tendon 4 will be stretched because it's lower end is not attached to the pivot point of the phalange 1 but to an element behind. This tension of the tendon will initiate movement of the second phalange. Similarly the movement of the third phalange will be initiated by the stretch of the second tendon upon movement of the second phalange. The length of the tendons as well as a shape of the lower back of the first and the second phalanges will determine amount of the stretch of the tendons and therefore will determine degree of the movement of the phalanges. The tension of the first tendon can be also adjusted by the down or up movement of the rod 7 and will apply mostly to the thumb finger because thumb for most of the grips, has a different timing for closing than remaining four fingers. It is believed that for all fingers the third phalanges degree of movement don't need any adjustments as they are moving in the strict relation with the second phalanges except for the thumb again. But in order to accommodate for the fundamental movements steering elements for all the fingers in the arm limited space, some secondary functions are intended to be abolished as the goal of this invention is not to create perfect human prosthetic hand but rather more simple, yet practical, reliable and affordable one.

FIG. 3

It shows first and second phalanges clevises and ears configuration at the pivot point. They are shaped to make a contact in the point P and keep phalanges in the straight position when open and prevent them from over bending by the action of the spring 8.

FIG. 4

It shows adjustable rod 7 and the lower end of tendon 4. It shows the one of many possible connections between them throughout pin 11 which is press fitted in the rod's clevis.

FIG. 5

Figure 1:
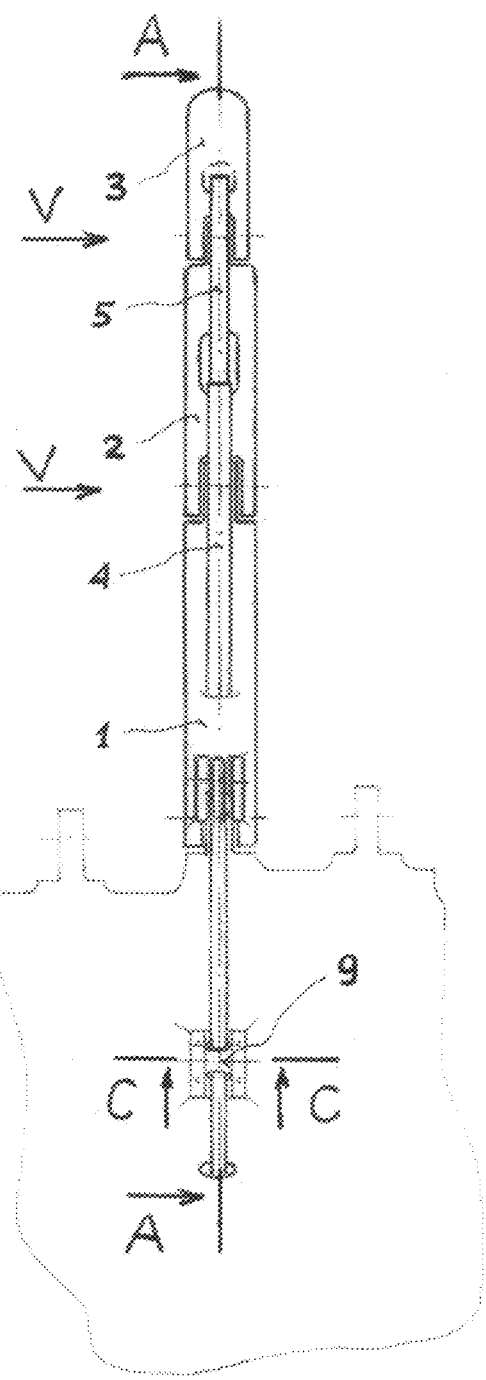
FIG. 1 is the front view of the finger without a flesh imitator.
Figure 7:
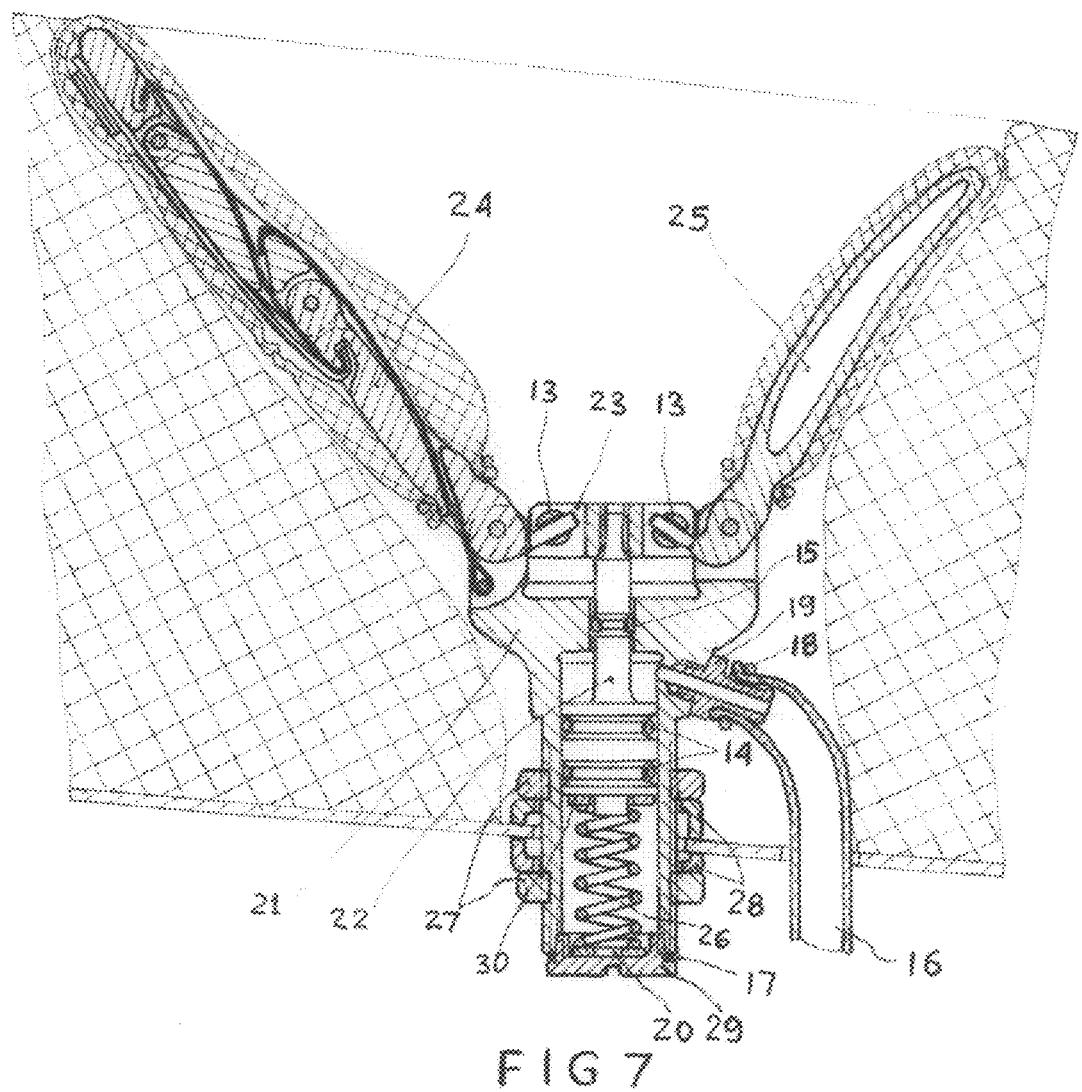
FIG. 7 is the main section of the massaging device.
Figure 8:
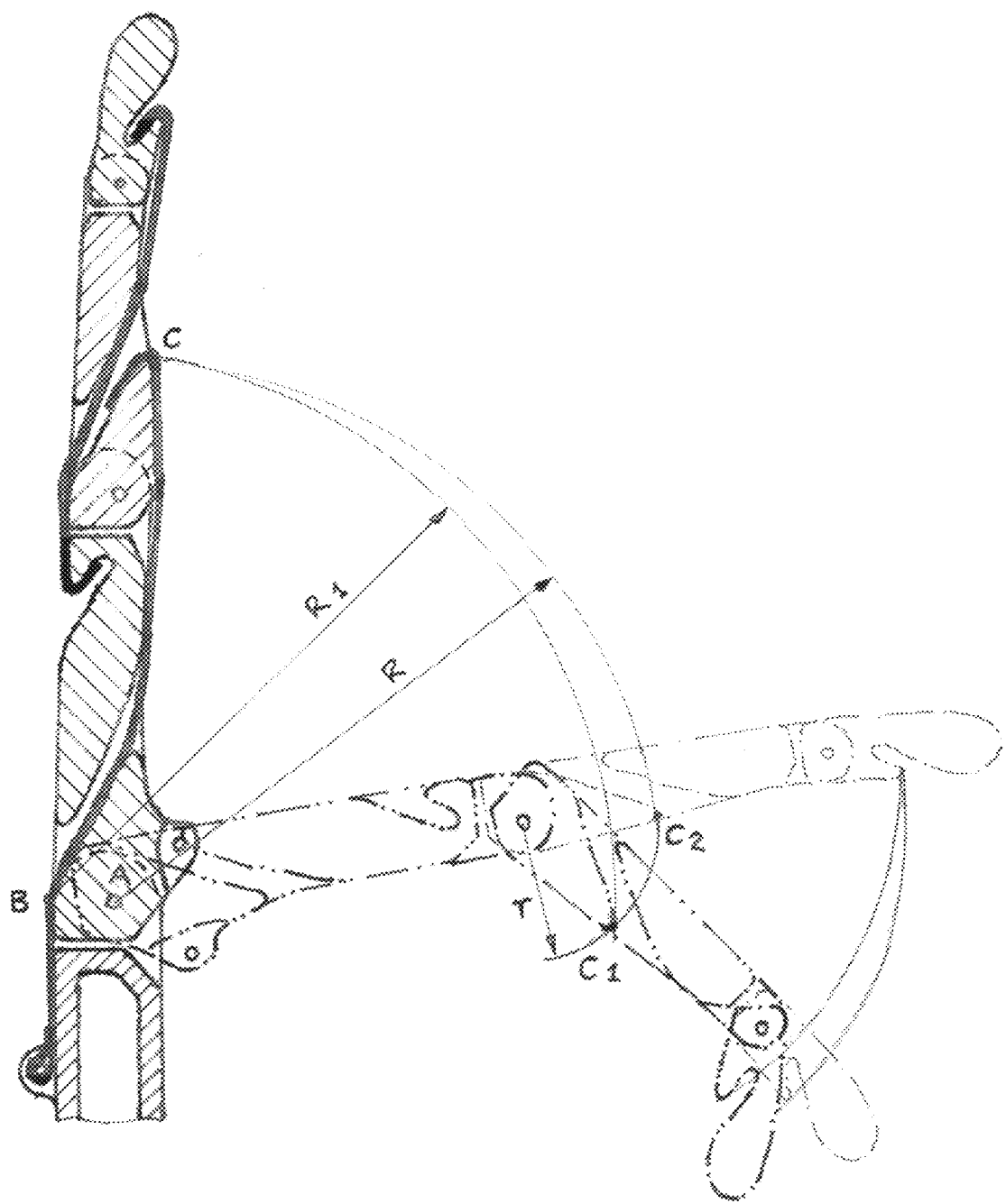
FIG. 8 is the view of the finger's skeleton in straight and in bent positions.

It is the section throughout guiding pin 9 and protruding across it activating rod 6 shown and described previously on FIG. 1. The same mechanism is used also in the massaging device FIG. 7 for connecting fingers 24 and 25 with disc 23.

FIG. 6

It is the cross section of the top of the third phalange 3. It shows slot at the back of phalange throughout which protrudes spring 8.

FIG. 7

It shows the massaging device installed in the back of the chair. It shows all the parts used and describes mechanics of said massaging device. Cylinder 21 is threaded on its outside bottom diameter and is fastened to chair's structure by nuts 27. Special washers 28 are having unparallel surfaces on both sides what allows to adjust device's mounting angle on the chair. Inside cylinder 21 is placed piston 22 sealed with O rings 14. The bottom boss of the piston 22 is out of round to accommodate for the gripping tool during assembly. Under the bottom of the piston is placed spring 26 and washers 20 and 30. Inner wall of the lower end of the cylinder 21 has thread to connect closing plug 29. Connection is sealed by gasket 17. In upper part of the cylinder there is threaded side hole in which is placed nozzle 19. Hose 16 is attached to the nozzle and secured by clip 18. Upper part of the cylinder 21 has a bigger diameter to accommodate for the fingers 24 and 25 as well as the driving disc 23. Said driving disc 23 is round and is guided with loose in the round opening made in the upper end of cylinder 21. Disc 23 has two slots opposite to each other and two round holes across the slots. In said across holes are placed with loose guiding pins 13 which have round holes across them. Disc 23 has a threaded hole in the centre and is connected through it with the rod of the piston 22. Cylinder 21 has a hole in the centre between the lower and the upper part of the body. Through this hole protrudes piston's 22 rod and it is sealed with the O ring 15. Two slots opposite to each other are made in the wall of the upper body of the cylinder 21. In those slots are placed fingers 24 and 25 which are connected to the body of said cylinder 21 with the pins press fitted in the across holes. This connection is the same one than between the finger and the palm structure and was earlier described on FIG. 1 and FIG. 2. Also the finger 24 is the same than earlier described on FIG. 1, FIG. 2, FIG. 3 and FIG. 6. The only difference is that the clevis to connect activating rod at the front of the lower end of first phalange is eliminated and this part of the phalange is shaped into the round pin. Those round pins placed at the bottom of the fingers 24 and 25 are protruding with loose through across holes of the guiding pins 13. Said guiding pins 13 are acting the same way than earlier described on FIG. 1 and FIG. 5 guiding pin 9. They will turn in their round holes of the disc 23 during up and down movement of said disc what will allow for sliding in them round bottom pins of the fingers 24 and 25 and therefore allow unrestricted movement of the fingers. Described above two fingers are intended to imitate pinching action of the thumb and the index or the thumb and the middle finger. One or two more slots can be added though to the upper wall of the cylinder 21 as well as to the driving disc 23 and one or two more fingers or specifically shaped claws can be accommodated into these slots. Such a device can be attached to a tip of mechanical arm or a manipulator. The presented here massaging device is powered preferably by pressurized air what will allow to install multiple units in a chair or other structure and operate them by a single pump. The air supplied through hose 16 will drive piston 22 down and together with it will drive down disc 23. Down movement of the disc 23 will create closing action of the finger 24 and finger 25 together with the bending action of the finger 24 as per previous description. The opening of the fingers is done by the action of compressed spring 26 upon release of the air pressure.

FIG. 8

It shows skeleton of the finger and both tendons in the straightened inactive position as well as a bare skeleton of the finger in the closing position. This figure is intended to clarify the fingers bending mechanism. The entire finger without tendons from the first upward position to the second lower position would rotate about point A. Point C of the second phalange where upper end of the first tendon attaches would move along the arc defined by radius R and in lower position would take location C2. Point C of the upper end of the first tendon will rotate about point B along the arc defined by radius R1 and in the lower position will take location C1 forcing therefore point C2 to move along the arc defined by radius r to the location C1 where the arcs of radius R1 and radius r intersect. The same principle applies toward rotation of the third phalange upon stretching of the second tendon and it is very characteristic to this design that top phalange will be bending spontaneously with the middle phalange just like in our human fingers where it is very difficult or impossible to bend middle digit without bending top digit at the same time.

The invention claimed is:

1. A mechanical finger comprising:
  a first phalange pivotally connected at a lower end to a mechanical palm;
  a second phalange pivotally connected at a lower end to an upper end of the first phalange;
  a third phalange pivotally connected at a lower end to an upper end of the second phalange, said first, second and third phalanges pivoting about parallel axes;
  a first tendon connected with one end to the palm or to an adjustable rod at a back and below the lower end of the first phalange and with the other end connected to the front of the second phalange above a pivotal point, said first tendon activating the second phalange upon movement of the first phalange;
  a second tendon connected with one end to the back of the first phalange and with the other end connected to the front of the third phalange above a pivotal point, said second tendon activating the third phalange upon movement of the second phalange;
  a second and a third phalanges straightening spring means firmly connected with one end to the back of the first phalange and a second free end of said spring being placed in a bracket located at the back of the third phalange;
  a driving rod means pivotally connected with one end to the front lower end of the first phalange and the second end of said rod being connectable to an actuator;
  wherein the adjustable rod is connectable with one end to the lower end of the first tendon and connectable to a second actuator with another end.

2. The mechanical finger of claim 1 wherein there is an opening in the middle of the first phalange throughout which said first tendon protrudes and analogically there is an opening in the middle of the second phalange throughout which the second tendon protrudes.

3. The mechanical finger of claim 1 wherein the actuation of the second phalange by the movement of the first phalange and the actuation of the third phalange by the movement of the second phalange results from the lower ends of respective tendons placed behind lower parts of the respective phalanges with some distance from their pivotal points therefore when the first phalange moves toward a horizontal position, the distance between a first tendon's connecting point to the second phalange and a point where lower part of the tendon contacts a lower back part of the first phalange will become greater than a distance between tendon's upper connection point and a pivotal point of the first phalange therefore rotation of said upper connection point about a second phalange pivotal axes will be initiated in order to compensate for said distances difference, analogically when the second phalange moves and stretches the second tendon it will force the third phalange to rotate about its pivotal axes characteristically to this design bending the third phalange spontaneously with the motion of the second phalange, wherein the amount of the second tendon tension is regulated by the distance between second phalange pivotal point and a lower back point of contact with a lower part of said tendon and also the first tendon's amount of the tension can be regulated this way when adjusting actuation is not being used.

4. The mechanical finger of claim 1, wherein the driving rod is connected to an actuator at said second end wherein up and down movements of the rod initiated by the actuator will cause rotation of the first phalange while the adjustable rod connects to the bottom end of the first tendon with one end and to a second actuator with another end to regulate tension of the first tendon in order to accommodate degree of rotation of the second phalange required for the certain grip.

5. A massaging device in combination with the mechanical finger of claim 1 comprising:
  a cylinder having a lower closed chamber and an upper open chamber; a piston placed in the cylinder's lower chamber; a driving disc placed in the cylinder's upper chamber and connected to a piston rod;
  said mechanical finger and one unbendable finger placed in slots and pivotally connected to an upper chamber's wall and also connected by bottom round pins to the driving disc;
  two pins placed across slots in a driving disc with across holes in them throughout which a driving disc is connected to the fingers;
  two beveled washers placed between two nuts attached by a thread to the outside wall of a lower part of a cylinder intended for the adjustment of cylinder's mounting angle;
  a returning spring placed in a lower chamber under a piston.

6. The massaging device in combination with the mechanical finger of claim 1, wherein up and down movement of the piston and the driving disc will cause pivotal movement of the fingers and create a pinching action of said fingers and simulate massaging effect of the thumb and the index finger or the thumb and the middle finger.

* * * * *